United States Patent [19]

Nogami et al.

[11] Patent Number: 5,474,924
[45] Date of Patent: * Dec. 12, 1995

[54] METHOD FOR PRODUCING 2-KETO-L-GULONIC ACID

[75] Inventors: Ikuo Nogami; Hideo Shirafuji, both of Nagaokakyo; Masahide Oka, Kawanishi; Takamasa Yamaguchi, Suita, all of Japan

[73] Assignee: Takeda Chemical Industries, Ltd., Japan

[ * ] Notice: The portion of the term of this patent subsequent to Oct. 31, 2007, has been disclaimed.

[21] Appl. No.: 438,999

[22] Filed: Nov. 22, 1989

Related U.S. Application Data

[63] Continuation of Ser. No. 913,230, Oct. 1, 1986, abandoned.

[30] Foreign Application Priority Data

Oct. 22, 1985 [JP] Japan .................................. 60-236857
Dec. 24, 1985 [JP] Japan .................................. 60-291472

[51] Int. Cl.⁶ .............................. C12P 7/60; C12N 1/20
[52] U.S. Cl. ......................... 435/138; 435/137; 435/422; 435/252.1
[58] Field of Search .................................. 435/138, 137, 435/874, 252.4, 252.1, 822

[56] References Cited

U.S. PATENT DOCUMENTS 3,043,749  7/1962  Huang ..................................... 435/138
3,234,105  2/1966  Motizuki et al. ......................... 195/49

FOREIGN PATENT DOCUMENTS 526660  1/1975  U.S.S.R. ................................ 435/138

OTHER PUBLICATIONS

Makover, et al., *Biotechnol. Bioeng.* 17(10) 1975, pp. 1485–1514.
Bergey's Manual of Sytematic Bacteriology, vol. 1, 1984, pp. 184–185.
Yin et al., "Acta Microbiologica Sinica", 20(3) 246–251 (1980).
Yan et al., "Acta Microbiologica Sinica", 21(2) 185–191 (1981).
Kanzaki et al., "Agr. Biol. Chem." 34(3), 43–436 (1970).
Tsukada et al., "Biotechnology and Bioengineering", vol. XIV, 799–810 (1972) John Wiley & Sons, New York (1972).

*Primary Examiner*—Irene Marx
*Attorney, Agent, or Firm*—Wenderoth, Lind & Ponack

[57] ABSTRACT

2-keto-L-gulonic acid is in high yield produced by contacting a microorganism of the genus Pseudogluconobacter, either as it is or after processing, with L-sorbose.

6 Claims, No Drawings

5,474,924

METHOD FOR PRODUCING 2-KETO-L-GULONIC ACID

This application is a continuation of now abandoned application Ser. No. 06/913,230, filed on Oct. 1, 1986, now abandoned.

The present invention relates to a method for producing 2-keto-L-gulonic acid which is of value as an intermediate for the synthesis of L-ascorbic acid and the strains of the genus Pseudogluconobacter to be used in the production method.

2-Keto-L-gulonic acid which is a valuable intermediate for the synthesis of L-ascorbic acid has heretofore been produced by the commercially established method of Reichstein [Helvetica Chimica Acta 17, 311 (1934)]. However, this method involves many steps, requires large quantities of solvents, and is therefore not satisfactory as a modern technology. As alternatives of this Reichstein's method, several methods employing microorganisms, in the main, have been proposed. For example, one may refer to the method which comprises oxidizing glucose to 5-keto-D-gluconic acid with the aid of a microorganism, reducing it either chemically or microbiologically to L-idonic acid, and oxidizing the same further microbiologically to 2-keto-L-gulonic acid [U.S. Pat. No. 2,421,611]. Another method that is known comprises oxidizing glucose to 2,5-diketo-D-gluconic acid with the aid of a microorganism and converting the same to 2-keto-L-gulonic acid microbiologically or chemically [Japanese Patent Publication No. 39-14493, No. 53-25033, No. 56-15877 and No. 59-35920].

However, the chemical reduction steps in these known methods, namely the reduction of 5-keto-D-gluconic acid to L-idonic acid in the former method and the reduction of 2,5-diketo-D-gluconic acid to 2-keto-L-gluonic acid in the latter method, have disadvantages in respect to stereo-specificity, so that the by-production of D-gluconic acid in the former and 2-keto-D-gluconic acid in the latter results in decreased yields of the desired compound. Furthermore, even when the above reduction is carried out with the aid of a microorganism, the overall product yield drops because the microorganism must be supplied with an excess of glucose (the starting material) as a reduction energy source. In this respect, the production of 2-keto-L-gulonic acid using L-sorbose as a starting material involves only an oxidation process. In fact, attempts using the bacterium belonging to the genus Gluconobacter, the genus Pseuckmonas, the genus Serratia, the genus Achromobacter and the genus Alcaligenes, have already been made in this direction. Thus, one may refer to the literatures including Biotechnology and Bioengineering 14, 799 (1972), Acta Microbiologica Sinica, 20, 246 (1980), and 21, 185 (1981), Japanese Patent Publication No. 41-159 and No. 41-160, U.S. Pat. No. 3,043,749 and Japanese Patent Publication No. 49-39838.

However, the results achieved with the strains so far named in the literature are not satisfactory, indeed, and the yields are too low to warrant a commercial exploitation of them.

Under the circumstances the present inventors sought earnestly for a commercially profitable method for producing 2-keto-L-gulonic acid and discovered that a bacterial strain K591s which was isolated from a soil sample collected in Wakayama Prefecture and bacterial strains 12-5, 12-15, 12-4 and 22-3 which were isolated from soil samples collected in Shiga Prefecture are able to convert L-sorbose to 2-keto-L-gulonic acid in yields by far exceeding the earlier results. Moreover, as the result of a taxonomical investigation, the present inventors found that these are new bacteria which have not been described in the literature. The present invention has been developed on the basis of the above findings.

Thus, the present invention is concerned with (1) a method for producing 2-keto-L-gulonic acid which comprises contacting a microorganism of the genus Pseudogluconobacter which is able to oxidize L-sorbose to 2-keto-L-gulonic acid, either as it is or after processing, with L-sorbose to produce and accumulate 2-keto-L-gulonic acid and harvesting the same; (2) a method for producing 2-keto-L-gulonic acid which comprises contacting a microorganism of the genus Pseudocluconobacter which is able to oxidize L-sorbose to 2-keto-L-gulconic acid with L-sorbose in the presence of at least one of the microorganisms belonging to the genus Bacillus, the genus Pseudomonas, the genus Proteus, the genus Citrobacter, the genus Enterobacter, the genus Erwinia, the genus Xanthomonas, the genus Flavobacterium, the genus Micrococcus, or the genus Escherichia; and (3) the *Pseudogluconobacter saccharoketogenes* which is aerobic and grows in the presence of coenzyme A.

Of the above-mentioned 5 bacterial strains, the strains K591s and 12-5 have the following taxonomical characteristics.

(a) Morphology
(1) Rods, which measure 0.3 to 0.5×0.7 to 1.4 μm.
(2) No cellular polymorphism
(3) Motile with 2 to 4 polar flagella
(4) Non-sporulating
(5) Gram-negative
(6) Non-acid-fast (b) Cultural characteristics
(1) Nutrient agar plate: Substantially no growth. Yeast extract nutrient agar: Round, entire margin, smooth surface, opalescent.
(2) Yeast extract nutrient agar slant: Growth moderate and filiform, smooth, opalescent.
(3) Yeast extract nutrient liquid culture: Moderate growth, uniform turbidity throughout medium.
(4) Nutrient gelatin stab: Sparse surface growth; gelatin not liquefied.
(5) Litmus milk: Acidified and coagulated.

(c) Physiological characteristics
(1) Nitrate reduction: weak but positive
(2) Denitrification: negative
(3) Methyl red (MR) test: positive
(4) Voges-Proskauer (VP) test: negative
(5) Indole: not produced
(6) Hydrogen sulfide: not produced
(7) Starch: not hydrolized
(8) Citric acid: not utilized
(9) Ammonium salts: utilized
(10) Pigments: not produced
(11) Urease: produced
(12) Oxidase: positive
(13) Catalase: positive
(14) The temperature range for growth: 16°–36° C.; the optimum temperature range for growth: 24°–34° C. The pH range for growth: 5.5–8.7; the optimum pH range: 6.0–7.5.
(15) Aerobic
(16) Hugh-Leifson's OF test: oxidative
(17) Acid is produced but gas is not produced from L-arabinose, D-xylose, D-glucose, D-fructose, D-galactose, D-mannose, maltose, sucrose, lactose, trehalose, D-mannitol, and glycerol. Neither acid nor gas is produced from D-sorbitol, inositol or starch (d) Other characteristics (1) Weak production of acetic acid from ethanol
(2) Biotin, thiamine, riboflavine and coenzyme A (CoA) are required for growth.
(3) Production of dihydroxyacetone from glycerol
(4) The guanine+cytosine content of DNA: 67±1 mole %
(5) The presence of a ubiquinone containing 10 isoprene units ($CoQ_{10}$)
(6) Marked production of 2-keto-L-gulonic acid from L-sorbose
(7) Streptomycin-resistant The taxonomical characteristics of the 12-15 strain are described below.
(a) Morphology
(1) Rod-shaped; cells measuring 0.3 to 0.5×0.7 to 1.4 μm
(2) No cellular polymorphism
(3) Motile with 2 to 4 polar flagella
(4) Non-sporulating
(5) Gram-negative
(6) Non-acid-fast
(b) Cultural characteristics
(1) Nutrient agar plate: Substantially no growth. Yeast extract nutrient agar plate: Round, entire margin, smooth and opalescent.
(2) Yeast extract nutrient agar slant: Growth moderate and filiform, smooth and opalescent.
(3) Yeast extract nutrient liquid culture: Moderate growth, uniform turbidity throughout medium.
(4) Nutrient gelatin stab: Sparse growth at top only. Gelatin not liquefied.
(5) Litmus milk: Acidified but not coagulated.
(c) Physiological characteristics
(1) Nitrate reduction: negative
(2) Denitrification: negative
(3) Methyl red (MR) test: positive
(4) Voges-Proskauer (VP) test: negative
(5) Indole: not produced
(6) Hydrogen sulfide: not produced
(7) Starch: not hydrolyzed
(8) Citrate: not utilized
(9) Ammonium salts: utilized
(10) No pigment production
(11) Urease: produced
(12) Oxidase: positive
(13) Catalase: positive
(14) Growth occurs at 23°–32° C., optimally at 28°–32° C. The pH range for growth: pH 6.0–7.5; the optimum pH range: 6.5–7.1.
(15) Aerobic
(16) Hugh-Leifson's of test: oxidative
(17) Acid is produced but gas is not produced from L-arabinose, D-xylose, D-glucose, D-fructose, D-mannose, maltose, sucrose, lactose, trehalose, and glycerol. Neither acid nor gas is produced from D-mannitol, D-sorbitol, inositol and starch.
(d) Other characteristics
(1) Weak production of acetic acid from ethanol
(2) Biotin, thiamine, riboflavine and CoA are required for growth
(3) Production of dihydroxyacetone from glycerol
(4) The guanine+cytosine content of DNA: 67±1 mole %
(5) The presence of a ubiquinone containing 10 isoprene units ($CoQ_{10}$)
(6) Marked production of 2-keto-L-gluonic acid from L-sorbose
(7) Streptomycin-resistant The taxonomical characteristics of the 12-4 strain are described below.
(a) Morphology
(1) Rods, each cell measuring 0.3 to 0.5×0.7 to 1.4 μm
(2) No cellular polymorphism
(3) Motile with 2 to 4 polar flagella
(4) Non-sporulating
(5) Gram-negative
(6) Non-acid-fast
(b) Cultural characteristics
(1) Nutrient agar plate: Minute colonies do not permit detailed observation. Yeast extract nutrient agar: Round, entire margin, smooth, opalescent.
(2) Yeast extract nutrient agar slant: Growth moderate and filiform, smooth, opalescent.
(3) Yeast extract nutrient liquid culture: Moderate growth; uniform turbidity throughout medium.
(4) Nutrient gelatin stab: Weak growth at top only. Gelatin not liquefied.
(5) Litmus milk: Acidified but not coagulated.
(c) Physiological characteristics
(1) Nitrate reduction: negative
(2) Denitrification: negative
(3) Methyl red (MR) test: positive
(4) Voges-Proskauer (VP) test: negative
(5) Indole: not produced
(6) Hydrogen sulfide: produced
(7) Starch: not hydrolyzed
(8) Citrate: not utilized
(9) Ammonium salts: utilized
(10) No pigment production
(11) Urease: produced
(12) Oxidase: positive
(13) Catalase: positive
(14) Growth occurs at 16°–36° C., optimally at 24°–34° C. The pH range for growth: 5.5–8.2; the optimum pH range: 6.0–7.5.
(15) Aerobic
(16) Hugh-Leifson's of test: oxidative
(17) Acid is produced but gas is not produced from L-arabinose, D-xylose, D-glucose, D-fructose, D-galactose, D-mannose, maltose, sucrose, lactose, trehalose, and glycerol. Neither acid nor gas is produced from D-mannitol, D-sorbitol, inositol and starch.
(d) Other characteristics
(1) Weak production of acetic acid from ethanol
(2) Biotin, thiamine, riboflavine and either CoA or pantothenic acid are required for growth.
(3) Production of dihydroxyacetone from glycerol
(4) The guanine+cytosine content of DNA: 67±1 mole %
(5) The presence of a ubiquinone containing 10 isoprene units ($CoQ_{10}$)
(6) Marked production of 2-keto-L-gulonic acid from L-sorbose
(7) Streptomycin-resistant The taxonomical characteristics of the 22-3 strain are described below.
(a) Morphology
(1) Rods, each cell measuring 0.3 to 0.5×0.7 to 1.4 μm.
(2) No cellular polymorphism
(3) Motile with 2 to 4 polar flagella
(4) Non-sporulating
(5) Gram-negative
(6) Non-acid-fast
(b) Cultural characteristics
(1) Nutrient agar plate: Minute colonies do not permit detailed observation. Yeast extract nutrient agar: Round, entire margin, smooth, opalescent.
(2) Yeast extract nutrient agar slant: Growth moderate and filiform, smooth, opalescent.

(3) Yeast extract nutrient liquid culture: Moderate growth; uniform turbidity throughout medium.
(4) Nutrient gelatin stab: Weak growth at top only. Gelatin not liquefied.
(5) Litmus milk: Acidified but not coagulated.
(c) Physiological characteristics
(1) Nitrate reduction: positive (weak)
(2) Denitrification: negative
(3) Methyl red (MR) test: positive
(4) Voges-Proskauer (VP) test: negative
(5) Indole: not produced
(6) Hydrogen sulfide: not produced
(7) Starch: not hydrolyzed
(8) Citrate: not utilized
(9) Ammonium salts: utilized
(10) No pigment production
(11) Urease: produced
(12) Oxidase: positive
(13) Catalase: positive
(14) Growth occurs at 16°–38° C. optimally at 24°–34° C. The pH range for growth: 5.5–8.7; the optimum pH range: 6.0–7.8.
(15) Aerobic
(16) Hugh-Leifson's OF test: oxidative
(17) Acid is produced but gas is not produced from L-arabinose, D-xylose, D-glucose, D-fructose, D-galactose, D-mannose, maltose, sucrose, lactose, trehalose, and glycerol. Neither acid nor gas is produced from D-mannitol, D-sorbitol, inositol and starch.
(d) Other characteristics
(1) Weak production of acetic acid from ethanol
(2) Biotin, thiamine, riboflavine and either CoA or pantothenic acid are required for growth.
(3) Production of dihydroxyacetone from glycerol
(4) The guanine+cytosine content of DNA: 67±1 mole %
(5) The presence of a ubiquinone containing 10 isoprene units ($CoQ_{10}$)
(6) Marked production of 2-keto-L-gulonic acid from L-sorbose
(7) Streptomycin-resistant The above taxonomical characteristics of the 5 strains of soil origin were reviewed by reference to Bergey's Manual of Determinative Bacteriology 8th ed. (1974) and Bergey's Manual of Systematic Bacteriology Vol 1 (1984). The above review showed that the K591s, 12-5, 12-15, 12-4 and 22-3 strains were tentatively classified into the genus Pseudomonas in view of the finding that they are gram-negative, motile, and rod bacteria having polar flagella. And in the light of the finding that they require certain growth factors, that the combined guanine and cytosine content of DNA is 67±1 mole % and that their quinone system is a ubiquinone having 10 isoprene units, they are similar to *Pseudomonas diminuta* and *Pseudomonas vesicularis* which belong to RNA Group IV of Section IV of this genus. However, the weak production of acetic acid from ethanol and the production of dihydroxyacetone from glycerol are the characteristics which differentiate the strains from the bacteria of the genus Pseudomonas.

The above characteristics are those of species of the genus Gluconobacter. However, in light of the fact that these 5 strains give positive responses to the oxidase test, are not able to grow at pH 4.5 and show good growth in either yeast extract nutrient medium or peptone yeast extract medium without carbohydrates, and have a combined DNA guanine and cytosine content of 67±1 mole %, they are different from the species of the genus Gluconobacter.

Thus, these 5 strains of K591s, 12-5, 12-15, 12-4 and 22-3 could not be relegated to any of the known genera and had to be considered to be bacteria of a novel species of a novel genus. Accordingly, the strains K591s, 12-5, 12-15, 12-4 and 22-3 were collectively designated as *Pseudogluconobacter saccharoketogenes*.

Referring to the nutritional requirements of these 5 strains, K591s, 12-5 and 12-15 have the unique property to require CoA for the growth. The CoA requirement of these 3 strains can not be substituted by pantothenic acid. On the other hand, 12-4 and 22-3 can grow in the presence of pantothenic acid as well as in the presence of CoA.

In the following description, these *Pseudogluconobacter saccharoketogenes* strains are sometimes referred to as oxidative strains.

The strains which can be used in accordance with the present invention include not only the above-described 5 strains but also other strains inclusive of the mutants derived from the 5 strains by irradiation with ultraviolet light or X-rays or treatment with chemical mutagens such as N-methyl-N'-nitro-N-nitrosoguanidine (nitrosoguanidine), methylmethanesulfonate, nitrogen mustard and so on. As an example of such mutants, there may be mentioned the strain TH 14-86 which was derived from *Pseudogluconobacter saccharoketogenes* K591s by treatment with nitrosoguanidine. This mutant strain TH 14-86 exhibits the same taxonomical characteristics as the parent strain except that it shows an increased ability to produce 2-keto-L-gulonic acid from L-sorbose.

The above-mentioned *Pseudogluconobacter saccharoketogenes* K591s, 12-5 and TH 14-86 were deposited at the Institute for Fermentation, Osaka, (IFO), 17-85 Jusohonmachi 2-chome, Yodogawa-ku, Osaka, Japan on Sep. 19, 1985 and *Pseudogluconobacter saccharoketogenes* 12-15, 12-4 and 22-3 on Dec. 16, 1985. Furthermore, *Pseudogluconobacter saccharoketogenes* K591s, 12-5 and TH 14-86 were deposited at Fermentation Research Institute (FRI) of the Agency of Industrial Science and Technology, the Ministry of International Trade and Industry, 1-3 Higashi 1-chome, Yatabe-machi tsukaba-gun, Ibaraki-ken 305, Japan on Oct. 7, 1985 and *Pseudogluconobacter saccharoketogenes* 12-15, 12-4 and 22-3 on Dec. 20, 1985. These deposits were converted to deposits under the Budapest Treaty and these microorganisms have been stored at FRI since Aug. 9, 1986.

The deposit numbers at IFO and at FRI are as follows:

| Microorganism | IFO | FRI | |
|---|---|---|---|
| Pseudogluconobacter saccharoketogenes K591s | 14464 | P-8481 | BP-1130 |
| Pseudogluconobacter saccharoketogenes 12-5 | 14465 | P-8480 | BP-1129 |
| Pseudogluconobacter saccharoketogenes TH14-86 | 14466 | P-8479 | BP-1128 |
| Pseudogluconobacter saccharoketogenes 12-15 | 14482 | P-8577 | BP-1132 |
| Pseudogluconobacter saccharoketogenes 12-4 | 14483 | P-8576 | BP-1131 |
| Pseudogluconobacter saccharoketogenes 22-3 | 14484 | P-8578 | BP-1133 |

In the practice of the present invention, the above-mentioned strains can be grown in L-sorbose-containing media or, alternatively, L-sorbose may be contacted with a preparation derived from cells of said strains.

The term "preparation derived from cells" or "cell preparation" is used herein to mean any and all of washed cells from culture broths of said bacteria, acetone dried cells, immobilized cells on supports such as polyacrylamide gel, K-carrageenin and the like, and other equivalent preparations.

The starting material L-sorbose may be added all at once at initiation of cultivation, in several installments in the course of cultivation or continuously to the culture medium.

Referring to the reaction by contact between L-sorbose and said microorganism, the concentration of L-sorbose in the reaction system is 3 to 30 percent (w/v), preferably 5 to 25% (w/v), based on the medium.

As an example of procedure for contacting L-sorbose with said bacterial cell preparation, there may be mentioned a method which comprises adding L-sorbose, 2-(N-morpholino) ethanesulfonic acid (MES) buffer (pH 6.5, 0.5M) and $CaCO_3$ to the cell preparation, diluting with water, and shaking the mixture in a conical flask.

The concentration of L-sorbose in such a reaction system for effecting contact between L-sorbose and said cell preparation is 0.1to 10% (w/v), preferably 0.3 to 3% (w/v). The amount of the cell preparation is 1 to 30 mg/ml on a pre-reaction dry cell basis. The pH of the reaction system is controlled in the range of pH about 5.5 to 7.5, the reaction temperature is about 20° to 40° C., and the reaction time is about 1 to 100 hours.

In working the present invention into practice by incubating a Pseudogluconobacter strain in an L-sorbose-containing liquid medium to produce and accumulate 2-keto-L-gluonic acid in the broth, it has been found that the accumulation yield of 2-keto-L-gulonic acid is remarkably higher when other bacteria are allowed to be present in combination with the Pseudogluconobacter oxidative strain than it is the case when the oxidative strain alone is cultivated.

The bacteria that are allowed to be present concomitantly may for example be bacteria of the following genera: Bacillus, Pseudomonas, Proteus, Citrobacter, Enterobacter, Erwinia, Xanthomonas and Flavobacterium. As the specific species, the following may be mentioned.

*Bacillus cereus* IFO 3131
*Bacillus licheniformis* IFO 12201
*Bacillus megaterium* IFO 12108
*Bacillus pumilus* IFO 12090
*Bacillus amyloliquefaciens* IFO 3022
*Bacillus subtilis* IFO 13719
*Bacillus circulans* IFO 3967
*Pseudomonas trifolii* IFO 12056
*Pseudomonas maltophilia* IFO 12692
*Proteus inconstans* IFO 12930
*Citorobacter freundii* IFO 13544
*Enterobacter cloacae* IFO 3320
*Erwinia herbicola* IFO 12686
*Xanthomonas pisi* IFO 13556
*Xanthomonas citri* IFO 3835
*Flavobacterium menigosepticum* IFO 12535
*Micrococcus varians* IFO 3765
*Escherichia coli* IFO 3366

Any of these stains may be incubated in an appropriate medium at 20° to 40° C. for 1 to 4 days and the resulting culture is used as an inoculum for cultivation in the presence of said concomitant bacteria. The inoculum size is generally desirably 1/10 to 1/1000 of that of the oxidative strain. When the concomitant strain in this amount is incubated with the oxidative strain, the growth of the oxidative strain is promoted so that compared with a pure culture of the oxidative strain, the mixed culture is able to oxidize L-sorbose in higher concentrations to 2-keto-L-gluonic acid in a shorter time period. The bacteria used as said concomitant bacteria are preferably these which cannot assimilate or only sparingly assimilate L-sorbose and 2-keto-L-gulonic acid. Otherwise, the same cultivation conditions as those of the pure culture of the oxidative strain can be employed. The medium used for cultivation of the above-mentioned microorganisms may be a liquid or solid medium containing nutrients which can be utilized by the said strain. However, for mass production, a liquid medium is preferred. The medium contains the carbon sources, nitrogen sources, inorganic salts, organic acid salts and trace nutrients which are generally used in the cultivation of microorganisms. While the starting material L-sorbose serves as the carbon source, other auxiliary carbon sources such as glucose, glycerin, sucrose, lactose, maltose, molasses, etc. can also be employed. The nitrogen sources are exemplified by various inorganic and organic nitrogen-containing compounds or nitrogenous materials such as ammonium salts (e.g. ammonium sulfate, ammonium nitrate, ammonium chloride, ammonium phosphate, etc.), corn steep liquor (CSL), peptone, meat extract, yeast extract, dried yeast, soybean flour, cottonseed meal, urea, and so on. As the inorganic salts, there may be employed salts of potassium, sodium, calcium, magnesium, iron, manganese, cobalt, zinc, copper and/or phosohoric acid.

As the trace nutrients, in addition to CoA, pantothenic acid, biotin, thiamine and riboflavine which are essential growth factors for said microorganisms, there can be added those substances which promote the growth of the microorganisms and the production of 2-keto-L-gulonic acid thereby, such as flavine mononucleotide (FMN), flavine adenine dinucleotide (FAD), other vitamins, L-cysteine, L-glutamic acid, sodium thiosulfate, etc., either in the form of pure chemical compounds or in the form of natural materials containing them, in suitable amounts.

As regards the cultural method, any of stationary culture, shaking culture, submerged culture, and so on can be employed. For mass production, the so-called submerged culture is preferred.

Of course, cultural conditions depend on the bacterial strain, medium composition, and other factors, and can be chosen in each case so that the object compound may be obtained with the highest efficiency. Thus, for example, the incubation temperature may advantageously be in the range of 25° to 35° C. and the medium pH may be about 5 to 9.

As the cultivation is conducted under the above conditions for 10 to 120 hours, 2-keto-L-gulonic acid is accumulated in the highest concentration. As the pH value of the medium generally lowers with the formation of the object compound, it may be advantageous to add a suitable basic substance such as sodium hydroxide, potassium hydroxide or ammonia from time to time so as to maintain the medium at an optimal pH level for the elaboration of 2-keto-L-gulonic acid by the bacterial strain or have a suitable buffer agent contained in the medium to thereby keep the medium pH constant.

Aside from the above, the sterilized culture broths of bacteria other than the oxidative strains can be used advantageously as medium components. The bacteria that can be utilized in this manner include those of the genus Bacillus, the genus Pseudomonas, the genus Citrobacter, the genus Escherichia, and the genus Erwinia, for instance. Specifically, the following bacteria may be mentioned.

| | | |
|---|---|---|
| *Bacillus cereus* | IFO | 3131 |
| *Bacillus subtilis* | IFO | 3023 |
| *Bacillus pumilus* | IFO | 12089 |
| *Bacillus megaterium* | IFO | 12108 |
| *Bacillus amyloliquefaciens* | IFO | 3022 |

| | | |
|---|---|---|
| Pseudomonas trifolii | IFO | 12056 |
| Citrobacter freundii | IFO | 12681 |
| Escherichia coli | IFO | 3546 |
| Erwinia herbicola | IFO | 12686 |

Thus, these bacteria are incubated in media which permit their growth at 20° to 40° C. for 2 to 4 days and the resulting culture broths are sterilized and added to the medium for the oxidative strain in a proportion of 0.5 to 5.0 percent (V/V). In this manner, growth of the oxidative strain can be encouraged.

The 2-keto-L-gulonic acid thus elaborated and accumulated in the culture broth or the reaction mixture can be harvested and purified by the per se known method utilizing its properties. 2-Keto-L-gulonic acid may be harvested in the form of free acid or separated in the form of salt with, for example, sodium, potassium, calcium, ammonium or the like.

Any harvesting method compatible with the object of the invention can be employed. For example, the culture broth is freed of cells, as required, by filtration, centrifugation or treatment with activated carbon and the solution is concentrated. The precipitated crystals are collected by filtration and recrystallized to recover the object compound. Further, solvent extraction, chromatography, precipitation or salting-out, and other procedures may be applied in a suitable combination and/or in repetition.

When 2-keto-L-gulonic acid is obtained in its free form, it can be converted to a salt with, for example, sodium, potassium, calcium, ammonium or the like by the conventional method. When the object compound is recovered in the form of a salt, it can be converted to the free acid or a different salt by the known method.

The identity of the product compound obtained by the method of the present invention with 2-keto-L-gulonic acid has been established by the determination of physicochemical constants such as elemental analysis, melting point, optical rotation, infrared absorption spectrum, etc.

The quantitative determination of 2-keto-L-gulonic acid in the reaction mixture or the culture broth was performed by high performance liquid chromatography (mobile phase: dilute sulfuric acid pH 2.2; flow rate: 0.5 ml/min.; detector: differential refractometer) using a sulfonated polystyrene gel column (Shimadzu Seisakusho, Ltd. , Japan, SCR-101H column, 7.9 mm×30 cm). As the standard, crystals of sodium 2-keto-L-gulonate monohydrate were used. The detection of 2-keto-L-gulonic acid was done by thin layer chromatography. Thus, as a cellulose plate (Merck, U.S.A.) was spotted with a sample and after development with a solvent system of phenol-water-formic acid (75:25:5) at room temperature for 3 hours, dried and treated with a color reagent, 2-keto-L-gulonic acid gave a spot at Rf about 0.30, the spot being black-brown with silver nitrate, yellow with o-phenylenediamine, or pink with anilinephthalic acid.

2-Keto-L-gulonic acid can be produced in good yield by the method of the present invention using a microorganism belonging to the genus Pseudogluconobacter which is able to oxidize L-sorbose to 2-keto-L-gulonic acid.

The following examples are intended to illustrate the present invention in further detail. The % figures mentioned in connection with media represent weight/volume percents.

Example 1

A 200 ml conical flask was charged with 20 ml of a seed culture medium containing 2.0% of glucose, 1.0% of peptone, 1.0% of dried yeast and 2.0% of $CaCO_3$ and sterilized by autoclaving at 120° C. for 20 minutes. The flask was inoculated with 1 loopful of *Pseudogluconobacter saccharoketogenes* K591s (IFO 14464; FERM BP-1130) grown on a slant medium in Table 1 at 28° C. for 4 days, and incubated at 30° C. with shaking (200 rpm) for 2 days. Two ml of the resulting broth was transplanted into a flask containing the same seed culture medium as above and incubated under the same conditions to give a seed culture.

A 200 ml conical flask was charged with 25 ml of a fermentation medium containing 2.0% of CSL, 0.5% of dried yeast, 0.5% of ammonium sulfate, 0.05% of $Na_2S_2O_3.5H_2O$, 0.2% of ferrous sulfate, 4.0% of $CaCO_3$, and 10.0% of L-sorbose (separately sterilized) and sterilized by autoclaving at 120° C. for 20 minutes. This conical flask containing the above fermentation medium was inoculated with 1.25 ml of the above-prepared seed culture and incubated with shaking at 30° C. for 3 days. As assayed by high performance liquid chromatography, the resulting fermentation broth contained 60.5 mg/ml of 2-keto-L-gluconic acid (conversion ratio: 56.1%). This fermentation broth (1000 ml) was centrifuged to remove the cellular and other sediments. The supernatant (980 ml) obtained was passed through an Amberlite IR 120 (Rohm & Haas Co., U.S.A., H-form, 500ml) column, which was then washed with about 300 ml of deionized water. The effluent and washings were combined and passed through an activated carbon (500 ml) column, followed by washing with about 300 ml of deionized water to remove the cations and color. The effluent and washings were combined (1600 ml), adjusted to pH 6.5 with sodium hydroxide, and concentrated under reduced pressure at 50° C. to about 70 ml. This concentrate rate was allowed to stand at 5° C. for 24 hours, whereupon colorless prisms were obtained. The prisms were collected by filtration, washed with a small quantity of cold methanol, and dried over phosphorus pentoxide at room temperature under reduced pressure to give 37.5 g of monosodium 2-keto-L-gulonate monohydrate.

Melting point 147°–155° C. (decomp.). Elemental analysis ($C_6H_9O_7Na.H_2O$) Calcd.: C, 30.78%; H, 4.74% Found: C, 30.94%; H, 4.85%

Optical rotation: $[\alpha]_D^{24}$ –23.3° (C=1.0, water). In HPLC retention time, TLC Rf value, and color, the above product was in agreement with the authentic sample.

Example 2

A test tube (16 mm×160 mm) containing 5 ml of a complete medium in Table 2 was inoculated with a loopful of *Pseudogluconobacter saccharoketogenes* K591s grown on a slant medium in Table 1 and incubated at 30° C. with shaking for 2 days. This culture (1 ml) was transferred to a test tube containing 5 ml of the same medium, which was then incubated with shaking for 4 hours. The resulting broth (5 ml) was aseptically centrifuged (12,000 rpm) at 5° C. for 15 minutes to harvest the cells. The cells were suspended in 10 ml of tris-maleic acid buffer (pH 6.5; 0.05M) and recentrifuged. The above procedure was repeated twice and the washed cells were suspended in 5 ml of the above-mentioned buffer containing 1 mg/ml of nitrosoguanidine and shaken at 30° C. for 2 hours for mutagenic treatment. The suspension was centrifuged (12,000 rpm) at 5° C. for 15 minutes to collect the cells which were then washed twice with 10 ml portions of trismaleic acid buffer to recover a fraction containing nitrosoguanidine-treated cells. This was diluted with 0.85% saline to a suitable concentration and spread over a plate (diameter: 9 cm) containing 15 ml of the complete medium (solid). The inoculated plate medium was incubated at 28° C. for 5 days to grow colonies. The colonies were counted and compared with the untreated control. The mortality of the microorganisms due to the nitrosoguanidine treatment was 90.4%. The colonies on the complete medium plate were replicated onto the minimum essential medium plates in Table 3 and after incubation at 28° C. for 3 days, the frequency of auxotrophs (nutritional mutants) was investigated. The frequency was about 6.6%.

The colonies treated with the mutagen on the complete medium plate were streaked onto a fresh complete medium plate over a length of about 2 cm at the rate of 12 strains per plate. After incubation at 28° C. for 2 days, one loopful of the grown cells were transferred to a test tube containing 3 ml of a medium (pH 6.5) composed of 7.0% of L-sorbose (separately sterilized), 1.0% of dried yeast 10% of peptone, 0 1% of ferrous chloride and 3.0% of $CaCO_3$ and incubated with shaking at 30° C. for 4 days. Among the tested mutant strains, the strain TH14-86 was found to produce 2-keto-L-gulonic acid twice as much as the parental strain K591s under the above conditions. This strain TH14-86 (IFO 14466; FERM BP-1128) was chosen as an oxidative strain with an augmented ability to oxidize L-sorbose.

TABLE 1

Slant medium (g/l)

| | |
|---|---|
| D-sorbitol | 25 |
| Peptone | 10 |
| Yeast extract | 10 |
| $CACO_3$ | 2 |
| Agar | 20 |
| pH 7.0 | |

TABLE 2

Complete medium (g/l)

| | |
|---|---|
| D-sorbitol | 25 |
| Peptone | 10 |
| Yeast extract | 10 |
| pH 6.5 (In the case of a solid medium, 20 g of agar was added) | |

TABLE 3

Minimum essential medium (g/l)

| | |
|---|---|
| Sucrose | 5 |
| $K_2HPO_4$ | 3 |
| $KH_2PO_4$ | 1 |
| $(NH_4)_2SO_4$ | 1 |
| NaCl | 1 |
| $MgSO_4.7H_2O$ | 0.1 |
| $MnCl_2.nH_2O$ | 0.002 |
| Sodium L-glutamate | 0.1 |
| L-cysteine | 0.1 |
| CoA | 0.002 |
| FMN | 0.002 |
| Thiamine | 0.002 |
| Biotin | 0.001 |
| pH 7.0 (In the case of a solid medium, 20 g of agar was added) | |

Example 3

The mutant strain TH14-86 derived from *Pseudoglucono-bacter saccharoketogenes* K591s in Example 2 was grown on a slant medium at 28° C. for 4 days. A loopful of the cells were taken from the slant culture and inoculated into a 200 ml conical flask containing 20 ml of the seed culture medium described in Example 1 and incubated at 30° C. with shaking for 2 days.

A conical flask of 1 liter capacity was charged with 200 ml of a medium composed of 3.0% of glucose, 1.0% of peptone, 1.0% of dried yeast and 2.0% of $CaCO_3$ and sterilized by autoclaving at 120° C. for 20 minutes. This conical flask was inoculated with 20 ml of the above culture and incubated at 28° C. with shaking for 2 days to give a seed culture. Separately, a loopful of *Bacillus megaterium* IFO 12108 grown on a slant medium at 28° C. for 2 days was inoculated into a 200 ml conical flask containing 20 ml of a medium composed of 4.0% of sucrose, 4.0% of cottonseed meal, 0.65% of $K_2HPO_4$, 0.55% of $KH_2PO_4$, 0.05% of ammonium sulfate, 0.05% of NaCl, 0.05% of magnesium sulfate and 0.05% of calcium pantothenate (pH 7.0) (sterilized by autoclaving at 120° C. for 20 minutes) and incubated at 30° C. for 3 days. The resulting culture broth was sterilized by autoclaving at 120° C. for 20 minutes, stored in the cold, and used as a component of the under-mentioned fermentation medium. Thus, a 5 liter jar fermentor was charged with 3 liters of a yeast medium composed of 12.5% of L-sorbose (separately sterilized at 120° C. for 15 minutes), 0.5% of ammonium sulfate, 0.03% of $KH_2PO_4$, 0.05% of $Na_2S_2O_3.5H_2O$, 0.05% of magnesium sulfate, 0.1% of $FeSO_4.7H_2O$, 5 µg/ml of $MnSO_4.4H_2O$, 5 µg/ml of thiamine, 0.1 µg/ml of biotin, 0.1 µg/ml of FMN, 5.0% of $CaCO_3$, and 4.0% (V/V) of the above sterilized broth of *Bacillus megaterium* and sterilized by autoclaving at 120° C. for 30 minutes. This fermentation medium was inoculated with 300 ml of the above seed culture and cultivated at 32° C. with aeration at 2.4N-l/min. and stirring at 800 r.p.m. for 3 days. The resultant fermentation broth contained 102.0 mg/ml of 2-keto-L-gulonic acid (conversion ratio: 75.7%). This broth (1 l) was purified in the same tanner as Example 1 to give 73.2 g of monosodium 2-keto-L-gulonate monohydrate crystals.

Example 4

*Pseudogluconobacter saccharoketogenes* 12-5 (IFO 14465; FERM BP-1129) was incubated in the same manner as Example 1 to give a seed culture. A 200 ml conical flask was charged with 20 ml of a fermentation medium (9.0% of L-sorbose) described in Example 3 and sterilized by autoclaving at 120° C. for 20 minutes. The flask was inoculated with 1.5 ml of the above seed culture and incubated at 32° C. for 2 days. The resulting fermentation broth contained 73.2 mg/ml of 2-keto-L-gulonic acid (conversion ratio: 75.4%).

Example 5

*Pseudogluconobacter saccharoketogenes* 12-4 (FERM BP-1131; IFO 14483), 12-15 (FERM BP-1132; IFO 14482) and 22-3 (FERM BP-1133; IFO 14484) were respectively incubated with shaking in the same manner as Example 4 for 3 days. The yields of 2-keto-L-gulonic acid in the broth were 52.1 mg/ml for the strain 12-4(conversion ratio: 53.7%); 48.7 mg/ml for the strain 12-15(conversion ratio:50.2%); and 69.3 mg/ml for the strain 22-3(conversion ratio:71.4%)

Example 6

A 200 ml conical flask was charged with 25 ml of a medium (pH 7.0) composed of 1.0% of L-sorbose (separately sterilized), 0.5% of peptone, and 0.5% of yeast extract and sterilized by autoclaving at 120° C. for 15 minutes. The flask was inoculated with a loopful of *Pseudogluconobacter saccharoketogenes* TH14-86 grown on a slant medium in Table 1 at 28° C. for 4 days and incubated at 30° C. with shaking for 2 days to give a seed culture.

A 200 ml conical flask was charged with 25 ml of a medium (pH 7.0) composed of 5.0% of L-sorbose (separately sterilized), 1.0% of peptone, 0.5% of yeast extract and 2.0% of $CaCO_3$ and sterilized by autoclaving at 120° C. for 15 minutes. This flask was inoculated with 1.0 m of the above seed culture and incubated at 30° C. for 2 days.

The resulting culture (500 ml) was allowed to stand at room temperature for 20 minutes and the sediment was removed by decantation. The remaining fluid was centrifuged at a slow speed of 1,000 rpm at room temperature to remove the sediment composed predominantly of $CaCO_3$. The cell suspension thus obtained was further centrifuged (6,000 rpm) at 5° C. for 10 minutes and the cells collected were washed twice with about 100 ml portions of cold saline (0.85%) and re-centrifuged (6,000 rpm) at 5° C. to give washed cells. The cells were further suspended in 35 ml of cold saline (0.85%) to give a washed cell suspension. To 4 ml of this washed cell suspension were added 300 mg of L-sorbose, 0.5 ml of 2- (N-morpholino)ethanesulfonic acid (MES) buffer (pH 6.5; 0.5M) and 180 mg of $CaCO_3$, followed by dilution with water to make 10 ml. The mixture was reacted in a 100 ml conical flask at 30° C. with shaking for 24 hours. The reaction mixture obtained in this manner was found to contain 24.6 mg/ml of 2-keto-L-gulonic acid-(conversion ratio: 76.0%).

Example 7

*Pseudogluconobacter saccharoketogenes* K591s, 12-5 and TH14-86 were respectively grown on a slant medium at 28° C. for 4 days. Separately, the concomitant bacteria in Table 4 were grown on the same slant medium at 28° C. for 2 days. One loopful of each strain was inoculated into a 200 ml conical flask containing 20 ml of a seed culture medium in Example 1 and incubated with shaking (200 rpm) at 30° C. for 2 days. In this manner, various culture broths were obtained.

A 200 ml conical flask was charged with 25 ml of a fermentation medium composed of 2.0% of CSL, 0.3% of dried yeast, 0.5% of ammonium sulfate, 0.05% of $Na_2S_2O_3.5H_2O$ 0.2% of ferrous sulfate, 5.0% of $CaCO_3$, and 15.0% of L-sorbose (separately sterilized) and sterilized by autoclaving at 120° C. for 20 minutes. The conical flask containing the above medium was inoculated with the above seed culture (1.5 ml) of one of said *Pseudogluconobacter saccharoketogenes* (oxidative) strains and incubated with shaking at 30° C. for 5 days to give a pure culture.

In the case of mixed culture, 0.1 ml of a seed culture of said concomitant bacteria was inoculated simultaneously at the inoculation with the oxidative strain and the inoculated medium was incubated at 30° C. with shaking for 5 days.

The amount of 2-keto-L-gulonic acid produced in each broth was assayed by high performance liquid chromatography. The results are set forth in Table 4. The presence of concomitant bacteria resulted in increased yields of 2-keto-L-gulonic acid.

TABLE 4

The production of 2-keto-L-gulonic acid by cultivation of the strain *Pseudogluconobacter saccharoketogenes* with and without the concomitant bacteria

| Concomitant Bacteria | *Pseudogluconobacter saccharoketogenes* | | |
|---|---|---|---|
| | K591s (mg/ml) | 12-5 (mg/ml) | TH14-86 (mg/ml) |
| No additive | 55.3 | 74.1 | 87.6 |
| | (34.2%) | (45.8%) | (54.1%) |
| *Bacillus cereus* | 87.3 | 101.5 | 125.9 |
| IFO 3131 | (54.0%) | (62.7%) | (77.8%) |
| *Bacillus licheniformis* | — | — | 125.0 |
| IFO 12201 | | | (77.3%) |
| *Bacillus megaterium* | 69.3 | 90.2 | 135.4 |
| IFO 12108 | (42.8%) | (55.8%) | (83.7%) |
| *Bacillus pumilus* | 93.1 | 129.0 | 134.7 |
| IFO 12090 | (57.5%) | (79.8%) | (83.3%) |
| *Bacillus amyloliquefaciens* | — | — | 126.9 |
| IFO 3022 | | | (78.5%) |
| *Bacillus subtilis* | 81.7 | 94.4 | 135.3 |
| IFO 13719 | (50.5%) | (58.4%) | (83.7%) |
| *Pseudomonas trifolii* | 67.2 | 98.8 | 122.6 |
| IFO 12056 | (41.5%) | (61.1%) | (75.8%) |
| *Pseudomonas maltophilia* | 71.9 | 79.8 | 135.3 |
| IFO 12692 | (44.4%) | (49.3%) | (83.7%) |
| *Proteus inconstans* | — | — | 124.5 |
| IFO 12930 | | | (77.0%) |
| *Citrobacter freundii* | — | — | 132.3 |
| IFO 13544 | | | (81.8%) |
| *Enterobacter cloacae* | — | — | 132.0 |
| IFO 3320 | | | (81.6%) |
| *Erwinia herbicola* | 71.8 | 111.6 | 129.1 |
| IFO 12686 | (44.4%) | (69.0%) | (79.8%) |
| *Xanthomonas pisi* | — | — | 121.5 |
| IFO 13556 | | | (75.1%) |
| *Flavobacterium meningosepticum* | — | — | 122.8 |
| IFO 12535 | | | (75.9%) |

The figure in the parenthesis shows a conversion ratio.

Example 8

A 2 l Sakaguchi flask was charged with 500 ml of a preculture medium composed of 2.0% of glucose, 1.0% of peptone, 1.0% of dried yeast, 2.0% of $CaCO_3$, and 0.01% of Actcol (defoaming agent, Takeda Chemical Industries, Ltd.) and sterilized by autoclaving at 120° C. for 20 minutes. The sells of *Pseudogluconobacter saccharoketogenes* TH14-86 grown on a slant medium in Table 1 were suspended in 10 ml of sterile water and the whole amount was inoculated into the Sakaguchi flask and incubated on a reciprocating shaker (85 spm) at 28° C. for 3 days to give a preculture. A 200-liter fermentor was charged with 120 l (pH 6.5) of a seed culture composed of 3.0% of glucose, 1.0% of CSL, 0.5% of dried yeast, 0.05% of sodium thiosulfate, 0.1% of ferrous sulfate, 2.0% of calcium carbonate and 0.03% of Actcol, and sterilized at 125° C. for 30 minutes. To this fermentor was transferred 1.8 l of the above-mentioned preculture, followed by cultivation at 120 rpm (agitation), 100N-l/min. (aeration), 1.0 Kg/cm$^2$ G(pressure) and 30° C. for 3 days to give a seed culture.

On the other hand, one loopful of the concomitant strain *Bacillus megaterium* IFO 12108 grown on a slant medium in Table 1 at 28° C. for 2 days was inoculated into a 2 liter Sakaguchi flask containing 500 ml of the above-mentioned preculture medium and incubated on a reciprocating shaker (85 spm) at 28° C. for 2 days to give a preculture. A 50 liter fermentor was charged with 30 l of the same medium as the above preculture medium and sterilized at 120° C. for 20 minutes. This fermentor was inoculated with 500 ml of the preculture of the concomitant strain and cultivated at 120 rpm (agitation), 30N-l/min. (aeration), 1.0 Kg/cm² G (pressure), and 30° C. for 2 days to give a seed culture of the concomitant strain.

A 2 m³ fermentor was charged with 1000 l of a fermentation medium composed of 15.0% of L-sorbose (separately sterilized), 5.0% of calcium carbonate, 2.0% of CSL, 0.2% of dried yeast, 0.3% of ammonium sulfate, 0.05% of sodium thiosulfate, 0.1% of ferrous sulfate, and 0.03% of Actcol and sterilized at 125° C. for 30 minutes. To this fermentor were transferred 110 l of the above seed culture of the strain *Pseudogluconobacter saccharoketogenes* TH14-86 and 10 l of the seed culture of the concomitant strain *Bacillus megaterium* IFO 12108, and the cultivation was carried out at 110 rpm (agitation), 900N-l/min. (aeration), 0.5 Kg/cm² G (pressure), and 30° C. The culture broth after 4 days of incubation contained 123.1 mg/ml of 2-keto-L-gulonic acid (conversion ratio: 76.1%).

Example 9

A 200 ml conical flask was charged with 20 ml of the preculture medium of Example 8 and sterilized by autoclaving at 120° C. for 30 minutes. A loopful of *Pseudogluconobacter saccharoketogenes* TH14-86 grown on a slant medium in Table 1 at 28° C. for 4 days was inoculated into the above flask and incubated at 30° C. with shaking for 2 days. The resulting culture (20 ml) was transferred to a 1 liter conical flask containing 200 ml of the same medium and incubated at 30° C. with shaking for 2 days to give a seed culture of TH 14-86.

One loopful of *Bacillus megaterium* IFO 12108 grown on a slant medium at 28° C. for 2 days was inoculated into a 200 ml conical flask containing 20 ml of the preculture medium and incubated with shaking at 28° C. for 2 days to give a seed culture of the concomitant bacteria. A fermentation medium (3 l) composed of 3.0% of L-sorbose (separately sterilized), 2.0% of CSL, 0.2% of dried yeast, 0.3% of ammonium sulfate, 0.05% of sodium thiosulfate, 0.1% of ferrous sulfate, 0.02% of Actcol and 9.0% of calcium carbonate was adjusted to 2.1 l and sterilized by autoclaving at 120° C. for 30 minutes. The sterilized medium was charged into a 5 liter jar fermenter.

This jar fermentor was inoculated with 300 ml of the above seed culture of the strain TH14-86 and 4 ml of the seed culture of the concomitant strain, and the cultivation was carried out at 30° C., 2.4N-l/min. (aeration) and 800 rpm (agitation).

Separately, 510 g of L-sorbose was dissolved in water to prepare 800 ml of a sorbose solution and sterilized by autoclaving at 120° C. for 20 minutes. This sterilized solution was continuously added to the jar fermentor from the 6th to the 42th hour of the cultivation. Following the addition of L-sorbose, the cultivation was continued under the same conditions as above for additional 28 hours (totally 70 hours). The resulting broth contained 163.5 mg/ml of 2-keto-L-gulonic acid (conversion ratio: 75.8%).

What we claim is:

1. A method for producing 2-keto-L-gulonic acid which comprises incubating a strain of *Pseudogluconobacter saccharoketogenes* selected from the group consisting of K591s, FERM BP-1130; TH 14-86, FERM BP-1128; 12-15, FERM BP 1132; 12-4, FERM BP-1131 and 22-3, FERM BP-1133, with L-sorbose to produce and accumulate 2-keto-L-gulonic acid and harvesting the accumulated 2 -keto-L-gulonic acid.

2. A method for producing 2-keto-L-gulonic acid which comprises incubating a strain of *Pseudogluconobacter saccharoketogenes* selected from the group consisting of K591s, FERM BP-1130; TH 14-86, FERM BP-1128; 12-15, FERM BP 1132; 12-4, FERM BP-1131 and 22-3, FERM BP-1133 with at least one microorganism selected from the group consisting of *Bacillus cereus* IFO 3131; *Bacillus licheniformis* IFO 12201; *Bacillus megaterium* IFO 12108; *Bacillus pumilus* IFO 12090; *Bacillus amyloliquefaciens* IFO 3022; *Bacillus subtilis* IFO 13719; *Pseudomonas trifolii* IFO 12056; *Pseudomonas maltophilia* IFO 12692; *Proteus inconstans* IFO 12930; *Citrobacter freundii* IFO 13544; *Enterobacter cloacae* IFO 3320; *Erwinia herbicola* IFO 12686; *Xanthomonas pisi* IFO 13556 and *Flavobacterium meningosepticum* IFO 12535, and further with L-sorbose to produce and accumulate 2-keto L-gulonic acid and harvesting the accumulated 2-keto-L-gulonic acid.

3. A biologically pure culture of a microorganism selected from the group consisting of *Pseudogluconobacter saccharoketogenes* K591s, FERM BP-1130; TH 14-86, FERM BP-1128; 12-15, FERM BP-1132; 12-4, FERM BP-1131 and 22-3, FERM BP-1133.

4. A method for producing 2-keto-L-gulonic acid which comprises incubating *Pseudogluconobacter saccharoketogenes* strain 12-5, FERM BP-1129 with L-sorbose to produce and accumulate 2 -keto-L-gulonic acid and harvesting the accumulated 2-keto-L-gulonic acid.

5. A method for producing 2-keto-L-gulonic acid which comprises incubating *Pseudogluconobacter saccharoketogenes* strain 12-5, FERM BP-1129, with at least one microorganism selected from the group consisting of *Bacillus cereus* IFO 3131; *Bacillus licheniformis* IFO 12201; *Bacillus megaterium* IFO 12108; *Bacillus pumilus* IFO 12090; *Bacillus amyloliquefaciens* IFO 3022; *Bacillus subtilis* IFO 13719; *Pseudomonas trifolii* IFO 12056; *Pseudomonas maltophilia* IFO 12692; *Proteus inconstans* IFO 12930; *Citrobacter freundii* IFO 13544; *Enterobacter cloacae* IFO 3320; *Erwinia herbicola* IFO 12686; *Xanthomonas pisi* IFO 13556 and *Flavobacterium meningosepticum* IFO 12535, and further with L-sorbose to produce and accumulate 2-keto-L-gulonic acid and harvesting the accumulated 2-keto-L-gulonic acid.

6. A biologically pure culture of the microorganism *Pseudogluconobacter saccharoketogenes* strain 12-5, FERM BP-1129.

* * * * *